United States Patent [19]

Denzel et al.

[11] 4,003,908
[45] Jan. 18, 1977

[54] DERIVATIVES OF IMIDAZO(4,5-b)PYRIDINES
[75] Inventors: Theodor Denzel, Regensburg; Hans Hoehn, Tegernheim, both of Germany
[73] Assignee: E. R. Squibb & Sons, Inc., Princeton, N.J.
[22] Filed: Mar. 11, 1976
[21] Appl. No.: 665,754
[52] U.S. Cl. .............. 260/295.5 B; 260/294.8 R; 424/266
[51] Int. Cl.² ........................................ C07D 213/55
[58] Field of Search .............. 260/295.5 B, 294.8 R
[56] References Cited

UNITED STATES PATENTS 3,840,546   10/1974   Hoehn et al. .............. 260/295.5 B
3,891,660   6/1975   Denzel et al. .............. 260/295.5 B Primary Examiner—Alan L. Rotman
Attorney, Agent, or Firm—Lawrence S. Levinson; Merle J. Smith

[57] ABSTRACT

Derivatives of imidazo[4,5-b]pyridines having the general formula

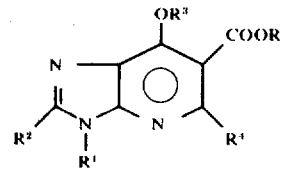

are disclosed. The novel compounds are useful as central nervous system depressants and anti-inflammatory agents.

14 Claims, No Drawings

DERIVATIVES OF IMIDAZO(4,5-b)PYRIDINES

SUMMARY OF THE INVENTION

This invention relates to new alkoxy-derivatives of imidazo [4,5-b]pyridines and salts of these compounds. These new compounds have the formula

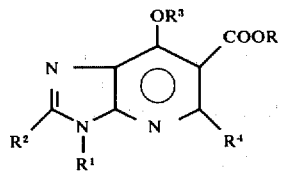
(I)

The symbols have the following meanings in formula I and through out this specification.

R is hydrogen or lower alkyl.

$R^1$ is hydrogen, lower alkyl, phenyl, phenyl-lower alkyl or cyclo-lower alkyl.

$R^2$ is hydrogen, lower alkyl, phenyl or phenyl-lower alkyl.

$R^3$ is lower alkyl, lower alkenyl, phenyl, substituted phenyl, i.e., the phenyl ring contains one or two simple substituents including lower alkyl, halogen, trifluoromethyl or amino, preferably one of the last three substituents, phenyl-lower alkyl or di-lower alkylamino-lower alkyl.

$R^4$ is hydrogen, lower alkyl or phenyl.

The lower alkyl groups in any of the foregoing radicals are straight or branched chain hydrocarbon groups of up to seven carbon atoms like methyl, ethyl, propyl, isopropyl and the like. The lower alkenyl are similar groups containing one double bond. Preferred are those with up to 4 carbons, specially those with 1 or 2 carbons. The di-lower alkylamino-lower alkoxy groups include lower alkyl and lower alkoxy radicals of the same type, preferably the $C_1$–$C_4$ members, e.g., dimethylaminopropoxy, dimethylaminoethoxy, diethylaminopropoxy, diethylaminoethoxy and the like. Preferably the lower alkoxy groups have two or more carbons, especially $C_2$–$C_4$-lower alkoxy.

The cyclo-lower alkyl groups include the $C_4$–$C_7$ alicyclics cyclobutyl, cyclopentyl, cyclohexyl and cycloheptyl, especially cyclopentyl and cyclohexyl.

The halogens include the four common halogens, especially chlorine and bromine.

The products of the examples which are representative of the various compounds of this invention constitute preferred embodiments. Preferably R is hydrogen or lower alkyl, especially ethyl; $R^1$ is lower alkyl, especially ethyl; $R^2$ is hydrogen or lower alkyl, especially hydrogen or methyl; $R^3$ is lower alkyl, especially ethyl; $R^4$ is lower alkyl or phenyl, especially methyl.

DETAILED DESCRIPTION

The new compounds of formula I are formed by the following series of reactions. The symbols in the structural formulas have the same meaning as previously described.

A 4,6-dihydroxypyridine carboxylic acid ester of the formula

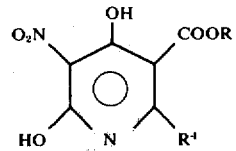
(II)

[produced analogous to the procedure described in Chem. Ber. 99, page 244, (1966)], is made to react with an inorganic acid chloride like phosphorous oxychloride, producing a compound of the formula

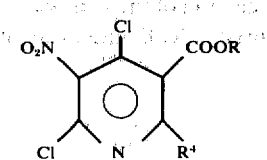
(III)

with the two chlorine atoms in the 4,6-position of the molecule.

This product is now treated with an appropriately substituted hydrazine of the formula

(IV)

By this reaction a compound of the formula

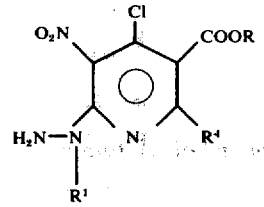
(V)

is obtained which is hydrogenated in the presence of a catalyst like Raney-Nickel, platinum or palladium on charcoal at room temperature. A compound of the formula

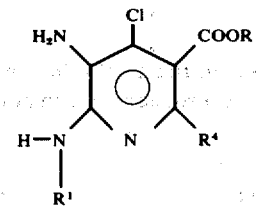
(VI)

is formed. Reaction of the compound of formula VI with an organic acid of the formula

(VII)

or with the corresponding ortho acid ester of the formula

(VIII)

results in the formation of a compound of the formula

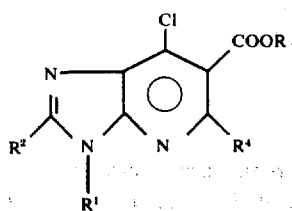

with a chlorine in the 4-position. The product of formula I is then produced by reaction of the compound of formula IX with the appropriate alcoholate or alcohol of the formulas

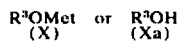

wherein Met is an alkali metal like sodium or potassium.

In an alternative procedure, a compound of formula I is produced by reaction of a compound of formula III with a secondary amine of the formula

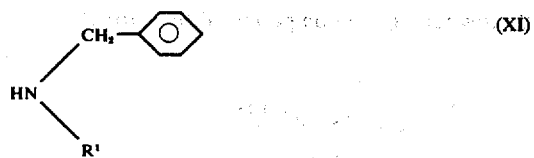

By this reaction, a compound of the formula

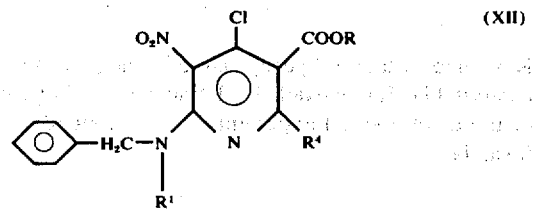

is formed, which is now made to react with the appropriate alcoholate of formula X, producing a compound of the formula

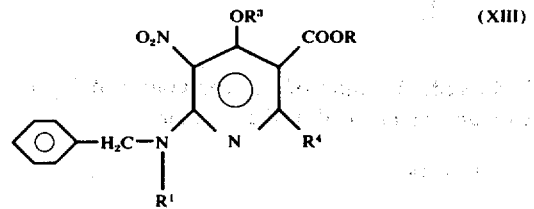

Hydrogenation of the compound of formula XIII in the presence of a catalyst like palladium on charcoal at a temperature in the range of 70°–80° C. and a hydrogen pressure of 2–3 atmospheres results in formation of a compound of the formula

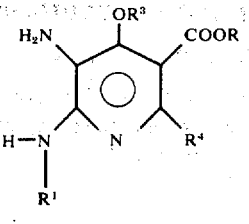

The compound of formula I is now obtained by treatment of the compound of formula XIV with the organic acid of formula VII or the ortho acid ester of formula VIII.

The compounds of formula I also form salts which are part of this invention. The salts include acid addition salts, particularly the non-toxic, physiologically acceptable members. These salts are formed by reaction, particularly of the ester (i.e., R is other than hydrogen), with one or more equivalents of any of a variety of inorganic and organic acids providing acid addition salts including, for example, hydrohalides (especially hydrochloride and hydrobromide), sulfate, nitrate, borate, phosphate, oxalate, tartrate, malate, citrate, acetate, ascorbate, succinate or aryl- or alkanesulfonates like benzenesulfonate, methanesulfonate, cyclohexanesulfamate and toluenesulfonate. The acid addition salts frequently provide a convenient means for isolating the product, e.g., by forming and precipitating a salt (which is not necessarily non-toxic) in an appropriate medium in which the salt is insoluble, then after separation of the salt, neutralizing with a base such as barium hydroxide or sodium hydroxide, to obtain the free base of formula I. Other salts can then be formed from the free base by reaction with one or more equivalents of acid containing the desired anion.

Certain members, particularly those compounds of formula I wherein R is hydrogen, form salts with metals, e.g., alkali metals like sodium, alkaline earth metals like calcium and magnesium, etc., by treatment of the acid with a base like sodium hydroxide or the like. These salts are useful to form soluble derivatives or as intermediates. They are also within the scope of the invention.

Additional experimental details are found in the examples.

The new compounds of this invention are psychotropic agents and can be used as ataractic agents for the relief of anxiety and tension states, for example, in mice, cats, rats, dogs and other mammalian species. For this purpose a compound or mixture of compounds of formula I, or nontoxic, physiologically acceptable salt thereof, is preferably administered orally, but parenteral routes such as subcutaneously, intramuscularly, intravenously or intraperitoneally in the described dosages, can also be employed. A single dose, or preferably 2 to 4 divided daily doses, provided on a basis of about 5 to 50 mg. per kilogram per day, preferably about 5 to 25 mg. per kilogram per day, is appropriate.

The new compounds of this invention also have antiinflammatory properties and are useful as anti-inflammatory agents, for example, to reduce local inflammatory conditions such as those of an edematous nature or resulting from proliferation of connective tissue in various mammalian species such as rats, dogs and the like when given orally in dosages of about 5 to 50 mg/kg/day, preferably 5 to 25 mg/kg/day, in single or 2 to 4 divided doses, as indicated by the carageean edema assay or delayed hypersensitivity reaction test in rats.

The compounds of the invention can be utilized by formulating in compositions such as tablets, capsules or elixirs for oral administration or in sterile solutions or suspensions for parenteral administration. About 5 to 250 mg. of a compound or mixture of compounds of formula I or physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which may be incorporated in tablets, capsules and the like are the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; a sweetening agent such as sucrose, lactose or saccharin; a flavoring agent such as peppermint, oil of wintergreen or cherry. When the dosage unit form is a capsule, it may contain in addition to materials of the above type a liquid carrier such as a fatty oil. Various other materials may be present as coatings or to otherwise modify the physical form of the dosage unit. For instance, tablets or capsules may be coated with shellac, sugar or both. A syrup or elixir may contain the active compound, sucrose as a sweetening agent, methyl and propyl parabens as preservatives, a dye and a flavoring such as cherry or orange flavor. Of course, any material used in preparing the dosage unit should be pharmaceutically pure and substantially non-toxic in the amounts employed.

For topical administration as an anti-inflammatory agent, a conventional lotion, ointment or cream containing about 0.1 to 3 percent by weight of a compound of formula I or its salt is formulated.

Injectables are formulated using as a vehicle water for injection or a natural or synthetic vegetable oil like sesame oil, peanut oil, cottonseed oil or the like or a synthetic like ethyl oleate. Preservatives, antioxidants, etc., are included as dictated by conventional pharmaceutical practice.

The following examples are illustrative of the invention and constitute especially preferred embodiments. They also serve as models for the preparation of other members of the group which can be produced by suitable substitution of starting materials. All temperatures are in degrees celsius.

EXAMPLE 1

7-Ethoxy-3-Ethyl-5-Methyl-3H-imidazo[4,5-b]Pyridine-6-Carboxylic Acid, Ethyl Ester a. 4,6-Dichloro-2-methyl-5-nitropyridine-3-carboxylic acid, ethyl ester 242 g. of 4,6-Dihydroxy-2-methyl-5-nitropyridine-3-carboxylic acid ethyl ester (1 mol.) are heated at 80° with 500 ml. of phosphorus oxychloride for 60 hours. After this time, the mixture is decomposed by pouring into ice water. The precipitate is filtered off and recrystallized from petroleum ether using charcoal to obtain 4,6-dichloro-2-methyl-5-nitropyridine-3-carboxylic acid ethyl ester, yield 195 g. (70%) m.p. 45°–46°.

b. 4-Chloro-6-(1-ethyl)hydrazino-2-methyl-5-nitropyridine-3-carboxylic acid, ethyl ester 27.9 g. of 4,6-Dichloro-2-methyl-5-nitropyridine-3-carboxylic acid ethyl ester (0.2 mol.) are dissolved in about 100 ml. of methanol and 20 ml. of water. 15 g. of triethylamine are added and at 25°–30° 4.5 g. ethyl hydrazine are dropped in with stirring. After the addition is complete, stirring is continued for 1 additional hour. On cooling, 4-chloro-6-(1-ethyl)hydrazino-2-methyl-5-nitropyridine-3-carboxylic acid, ethyl ester precipitates, yield 19.7 g. (65%) m.p. 117°–120°.

c. 5-Amino-6-ethylamino-4-chloro-2-methylpyridine-3-carboxylic acid, ethyl ester 30.3 g. of 4-chloro-6-(1-ethyl)hydrazino-2-methyl-5-nitropyridine-3-carboxylic acid, ethyl ester (0.1 mol.) are hydrogenated in 100 ml. of butanol with Raney-Nickel as catalyst at ordinary pressure until the theoretical amount of hydrogen has been absorbed (9 ltr.). The catalyst is filtered off and the solvent is removed in vacuo. The residue is treated with 300 ml. of ether using charcoal. After filtration, the ether is removed and the residue distilled in vacuo to obtain 5-amino-6-ethylamino-4-chloro-2-methylpyridine-3-carboxylic acid, ethyl ester, b.p. 190°–200°/0.01. Yield 18 g. (70%).

d. 7-Chloro-3-ethyl-5-methyl-3H-imidazo[4,5-b]pyridine-6-carboxylic acid, ethyl ester 25.7 g. of 5-amino-6-ethylamino-4-chloro-2-methylpyridine-3-carboxylic acid, ethyl ester (0.1 mol.) is refluxed for 12 hours with 100 ml. of orthoformic acid triethyl ester with stirring. The excess ester is removed in vacuo and the oily residue distilled to obtain 7-chloro-3-ethyl-5-methyl-3H-imidazo[4,5-b]pyridine-6-carboxylic acid, ethyl ester, b.p. 195°0.01. Yield 23 g. (86%).

e. 7-Ethoxy-3-ethyl-5-methyl-3H-imidazo[4,5-b]pyridine-6-carboxylic acid, ethyl ester 5.4 g. of 7-chloro-3-ethyl-5-methyl-3H-imidazo[4,5-b]-pyridine-6-carboxylic acid, ethyl ester (0.02 mol.) are added with stirring to a solution of 0.06 g. of sodium in 20 ml. of dry ethanol. The mixture is refluxed for 10 hours, the inorganic precipitate filtered off, the solvent removed in vacuo and the residue, 7-ethoxy-3-ethyl-5-methyl-3H-imidazo[4,5-b]pyridine-6-carboxylic acid, ethyl ester is crystallized with ether. Yield 4.1 g. (73%) m.p. 63°–65° (petroleum ether). The ester is dissolved in alcohol and ethanolic HCl is added. The precipitation is completed by the addition of ether. The solid is filtered off to obtain the hydrochloride salt.

EXAMPLE 2

3,5-Dimethyl-7-Ethoxy-3H-Imidazo[4,5-b]Pyridine-6-Carboxylic Acid, Ethyl Ester a.
4-Chloro-6-(1-methyl)hydrazino-2-methyl-5-nitropyridine-3-carboxylic acid ethyl ester 27.9 g. of 4,6-dichloro-2-methyl-5-nitropyridine-3-carboxylic acid ethyl ester (0.1 mol.) are dissolved in about 100 ml. methanol. At 50° C., 9.2 g. of methylhydrazine are dropped in and the mixture is stirred for 30 minutes. On cooling 4-chloro-6-(1-methyl)hydrazine-2-methyl-5-nitropyridine-3-carboxylic acid ethyl ester precipitates. Yield 18 g. (62.2%), m.p. 159°–161° (methanol).

b.
5-Amino-6-methylamino-4-chloro-2-methylpyridine-3-carboxylic acid ethyl ester 28.6 g. of 4-chloro-6-(1-methyl)hydrazino-2-methyl-5-nitropyridine-3-carboxylic acid ethyl ester is hydrogenated in 100 ml. butanol with Raney-Nickel as catalyst at 3 atmospheres of hydrogen pressure and 90°. When the hydrogen absorption ceases, the reaction is finished, the catalyst is filtered off and the solvent removed in vacuo. Distillation of the residue yields 22 g. of 5-amino-6-methylamino-4-chloro-2-methylpyridine-3-carboxylic acid ethyl ester (91%), b.p. 0.05 200°–210°.

c.
7-Chloro-3,5-dimethyl-3H-imidazo[4,5-b]pyridine-6-carboxylic acid ethyl ester 2.4 g. of 5-Amino-6-methylamino-4-chloro-2-methylpyridine-3-carboxylic acid ethyl ester (0.01 mol.) and 10 ml. of orthoformic acid triethyl ester are refluxed for 12 hours. After the excess ortho ester has been removed, the residue is recrystallized from ethyl acetate to obtain 7-chloro-3,5-dimethyl-3H-imidazo[4,5-b]pyridine-6-carboxylic acid ethyl ester, m.p. 56°–58°. Yield 2.2 g. (88%).

d.
3,5-Dimethyl-7-ethoxy-3H-imidazo[4,5-b]pyridine-6-carboxylic acid ethyl ester By replacing 7-chloro-3-ethyl-5-methyl-3H-imidazo[4,5-b]pyridine-6-carboxylic acid, ethyl ester in Example 1 e with 7-chloro-3,5-dimethyl-3H-imidazo[4,5-b]pyridine-6-carboxylic acid ethyl ester, 3,5-dimethyl-7-ethoxy-3H-imidazo-[4,5-b]pyridine-6-carboxylic acid, ethyl ester is obtained. Yield 78%, m.p. 85°–87° (ether).

EXAMPLE 3

3-Butyl-7-Ethoxy-5-Methyl-3H-imidazo[4,5-b]Pyridine-6-Carboxylic Acid, Ethyl Ester a.
6-(1-Butyl)hydrazino-4-chloro-2-methyl-5-nitropyridine-3-carboxylic acid, ethyl ester By replacing ethyl hydrazine in Example 1 b with butyl hydrazine, 6-(1-butyl)hydrazino-4-chloro-2-methyl-5-nitropyridine-3-carboxylic acid, ethyl ester is obtained. Yield 62%, m.p. 59°–61° (diethyl ether).

b.
5-Amino-6-butylamino-4-chloro-2-methylpyridine-3-carboxylic acid, ethyl ester By replacing 4-chloro-6-(1-ethyl)hydrazino-2-methyl-5-nitropyridine-3-carboxylic acid, ethyl ester in Example 1 c with 6-(1-butyl)hydrazino-4-chloro-2-methyl-5-nitropyridine-3-carboxylic acid ethyl ester, 5-amino-6-butylamino-4-chloro-2-methylpyridine-3-carboxylic acid, ethyl ester is obtained. Yield 72%, b.p. 200°–210°/0.01.

c.
3-Butyl-7-chloro-5-methyl-3H-imidazo[4,5-b]pyridine-6-carboxylic acid, ethyl ester By replacing 5-amino-6-ethylamino-4-chloro-2-methylpyridine-3-carboxylic acid, ethyl ester in Example 1 d with 5-amino-6-butylamino-4-chloro-2-methylpyridine-3-carboxylic acid, ethyl ester, 3-butyl-7-chloro-5-methyl-3H-imidazo[4,5-b]-pyridine-6-carboxylic acid, ethyl ester is obtained. Yield 83%, b.p. 190°–200°10/01.

d.
3-Butyl-7-ethoxy-5-methyl-3H-imidazo[4,5-b]pyridine-6-carboxylic acid, ethyl ester By replacing 7-chloro-3-ethyl-5-methyl-3H-imidazo[4,5-b]pyridine-6-carboxylic acid ethyl ester in Example 1 e with 3-butyl-7-chloro-5-methyl-3H-imidazo[4,5-b]pyridine-6-carboxylic acid, ethyl ester, 3-butyl-7-ethoxy-5-methyl-3H-imidazo[4,5-b]pyridine-6-carboxylic acid, ethyl ester is obtained. Yield 81%, b.p. 200°–210°/0.01. An equivalent of aqueous sodium hydroxide is added to an ethanol solution of the ethyl ester and refluxed for 1 hour. The reaction mixture is then taken to dryness, the residue is suspended in water and HCl to pH 4 is added. The precipitated solid is filtered off to obtain the free carboxylic acid. The sodium salt is obtained by dissolving this product in one equivalent of aqueous sodium hydroxide and freeze drying.

EXAMPLE 4

3,5-Dimethyl-7-(3-Methylbutoxy)-3H-Imidazo[4,5-b]Pyridine-6-Carboxylic Acid, Ethyl Ester 0.3 g. of sodium hydride are suspended in 100 ml. of anhydrous benzene. The mixture is heated with stirring at reflux temperature while 8.8 g. of 3-methylbutane-1-ol are dropped in. After the addition is completed, the mixture is refluxed for an additional 10 hours. After this time 25.3 g. of 7-chloro-3,5-dimethyl-3H-imidazo[4,5-b]pyridine -6-carboxylic acid, ethyl ester obtained in Example 2 c are added and refluxing is continued for 12 hours. The inorganic precipitate is filtered off and the solvent removed in vacuo. The oily residue is dissolved in 50 ml. of ether and, on cooling, 3,5-dimethyl-7-(3-methylbutoxy)-3H-imidazo[4,5-b]-pyridine-6-carboxylic acid, ethyl ester is obtained. Yield 24.3 g. (80%), m.p. 64°–66° (diethyl ether).

EXAMPLE 5

7-Butoxy-3-Butyl-5-Methyl-3H-Imidazo[4,5-b]Pyridine-6-Carboxylic Acid, Ethyl Ester 0.03 g. of sodium and 0.8 g. of n-butyl alcohol are refluxed for 5 hours in 50 ml. of dry benzene. After this time, 3 g. of 3-butyl-7-chloro-5-methyl-3H-imidazo[4,5-b]-pyridine-6-carboxylic acid, ethyl ester obtained in Example 3 c are added and the mixture is refluxed for 12 hours. After the inorganic precipitate has been filtered off, the solvent is removed in vacuo and the residue distilled to obtain 7-butoxy-3-butyl-5-methyl-3H-imidazo[4,5-b]pyridine-6-carboxylic acid, ethyl ester, b.p. 210°–220°/0.01. Yield 2.1 g. (66%).

EXAMPLE 6

3-Butyl-7-(3-Methylbutoxy)-5-Methyl-3H-Imidazo[4,5-b]Pyridine-6-Carboxylic Acid, Ethyl Ester By replacing n-butyl alcohol of Example 5 with 3-methyl-butane-1-ol, 3-butyl-7-(3-methylbutoxy)-5-methyl-3H-imidazo-[4,5-b]pyridine-6-carboxylic acid, ethyl ester is obtained, yield 72%, b.p. 200°–210°/0.01.

EXAMPLE 7

3-Butyl-7-(1-Methylethoxy)-5-Methyl-3H-Imidazo[4,5-b]pyridine-6-Carboxylic Acid, Ethyl Ester By replacing n-butyl alcohol in Example 5 with propane-2-ol, 3-butyl-7-(1-methylethoxy)-5-methyl-3H-imidazo[4,5-b]-pyridine-6-carboxylic acid, ethyl ester is obtained. Yield 68%, b.p. 195°–200°/0.01.

EXAMPLE 8

7-Ethoxy-2,3,5-Trimethyl-3H-Imidazo[4,5-b]Pyridine-6-Carboxylic Acid, Ethyl Ester a.

7-Chloro-2,3,5-trimethyl-3H-imidazo[4,5-b]pyridine-6-carboxylic acid, ethyl ester By replacing orthoformic acid triethyl ester in Example 1d with ortho acetic acid triethyl ester, 7-chloro-2,3,5-trimethyl-3H-imidazo[4,5-b]pyridine-6-carboxylic acid, ethyl ester is obtained. Yield 81%, m.p. 73°–75° (diethyl ether).

b.

7-Ethoxy-2,3,5-trimethyl-3H-imidazo[4,5-b]pyridine-6-carboxylic acid, ethyl ester By replacing 7-chloro-3-ethyl-5-methyl-3H-imidazo-[4,5-b]pyridine-6-carboxylic acid, ethyl ester in Example 1 e with 7-chloro-2,3,5-trimethyl-3H-imidazo[4,5-b]pyridine-6-carboxylic acid, ethyl ester of part a, 7-ethoxy-2,3,5-trimethyl-3H-imidazo[4,5-b]pyridine-6-carboxylic acid, ethyl ester is obtained. Yield 79%, m.p. 85°–87° (diethyl ether).

EXAMPLE 9

2,3,5-Trimethyl-7-(3-Methylbutoxy)-3H-Imidazo[4,5-b]Pyridine-6-Carboxylic Acid, Ethyl Ester By replacing 7-chloro-3,5-dimethyl-3H-imidazo[4,5-b]-pyridine-6-carboxylic acid, ethyl ester in Example 4 with 7-chloro-2,3,5-trimethyl-3H-imidazo[4,5-b]pyridine-6-carboxylic acid, ethyl ester of Example 8 a, 2,3,5, trimethyl-7-(3-methylbutoxy)-3H-imidazo[4,5-b]pyridine-6-carboxylic acid, ethyl ester is formed. Yield 58%, b.p. 195°–200°/0.01.

EXAMPLE 10

7-Butoxy-3,5-Dimethyl-3H-Imidazo[4,5-b]Pyridine-6-Carboxylic Acid, Ethyl Ester

By replacing 3-butyl-7-chloro-5-methyl-3H-imidazo[4,5-b]-pyridine-6-carboxylic acid, ethyl ester in Example 5 with 7-chloro-3,5-dimethyl-3H-imidazo[4,5-b]pyridine-6-carboxylic acid, ethyl ester of Example 2 c, 7-butoxy-3,5-dimethyl-3H-imidazo[4,5-b]pyridine-6-carboxylic acid, ethyl ester is formed. Yield 61%, b.p. 180°–190°/0.01.

EXAMPLE 11

3,5-Dimethyl-7-(1-Methylethoxy)-3H-Imidazo[4,5-b]Pyridine-6-Carboxylic Acid, Ethyl Ester When n-butyl alcohol is replaced by propane-2-ol and 7-chloro-3,5-diamethyl-3H-imidazo[4,5-b]pyridine-6-carboxylic acid, ethyl ester is processed as described for 3-butyl-7-chloro-5-methyl-3H-imidazo[4,5-b]pyridine-6-carboxylic acid, ethyl ester in Example 5,3,5-dimethyl-7-(1-methylethoxy)-3H-imidazo[4,5-b]pyridine-6-carboxylic acid ethyl ester is obtained. Yield 67%, b.p. 170°–175°/0.01. The free acid is obtained as described in Example 9. The potassium salt is obtained by substituting potassium hydroxide for sodium hydroxide in that example.

EXAMPLE 12

3-Ethyl-5-Methyl-7-(1-Methylethoxy)-3H-Imidazo[4,5-b]Pyridine-6-Carboxylic Acid, Ethyl Ester 0.03 g. of sodium hydride and 0.6 g. of propane-2-ol are refluxed with stirring in 50 ml. dry benzene for 10 hours. After this time, 2.7 g. of 7-chloro-3-ethyl-5-methyl-3H-imidazo[4,5-b]pyridine-6-carboxylic acid, ethyl ester obtained in Example 1 d are added and heating is continued for an additional 10 hours. The inorganic precipitate is filtered off and the solvent removed by distillation. The oily residue is distilled to obtain 3-ethyl-5-methyl-7-(1-methylethoxy)-3H-imidazo[4,5-b]pyridine-6-carboxylic acid, ethyl ester, b.p. 180°–185°/0.05. Yield 2 g. (69%).

EXAMPLE 13

7-Butoxy-3-Ethyl-5-Methyl-3H-Imidazo[4,5-b]Pyridine-6-Carboxylic Acid, Ethyl Ester By replacing propane-2-ol in Example 21 with butane-4-ol, 7-butoxy-3-ethyl-5-methyl-3H-imidazo[4,5-b]pyridine-6-carboxylic acid, ethyl ester is obtained. Yield 59%, b.p. 185°–190°/0.01.

EXAMPLE 14

3-Ethyl-5-Methyl-7-(3-Methylbutoxy)-3H-Imidazo[4,5-b]Pyridine-6-Carboxylic Acid, Ethyl Ester By replacing propane-2-ol in Example 12 with 3-methylbutane-1-ol, 3-ethyl-5-methyl-7-(3-methylbutoxy)-3H-imidazo[4,5-b]pyridine-6-carboxylic acid, ethyl ester is obtained. Yield 71%, b.p. 185°–190°/0.01.

EXAMPLE 15

2,5-Dimethyl-7-Ethoxy-3-Ethyl-3H-Imidazo[4,5-b]Pyridine-6-Carboxylic Acid, Ethyl Ester a.

4-Chloro-6-(N-benzyl-N-ethyl)amino-2-methyl-5-nitropyridine-3-carboxylic acid, ethyl ester 24.2 g. of 4,6-dichloro-2-methyl-5-nitropyridine-3-carboxylic acid, ethyl ester (0.1 mol.) of Example 1 a are dissolved in 200 ml. of alcohol and, after addition of 10.1 g. of triethylamine, the solution is heated at reflux temperature with stirring. At this point, 13.5 g. of benzylethylamine are dropped in. After the addition is completed, the mixture is refluxed for 2 additional hours and then evaporated to dryness. The residue is extracted with 200 ml. of hot ethyl acetate and the hydrochloride is filtered off. Removal of the solvent in vacuo yields a light yellow oil, 4-chloro-6-(N-benzyl-N-ethyl)amino-2-methyl-5-nitropyridine-3-carboxylic acid, ethyl ester which is purified by distillation. Yield 28 g. (74.2%), b.p. 0.1 195°–215°.

b.
6-(N-benzyl-N-ethyl)amino-4-ethoxy-2-methyl-5-nitropyridine-3-carboxylic acid, ethyl ester 19 g. of 4-chloro-6-(N-benzyl-N-ethyl)amino-2-methyl-5-nitropyridine-3-carboxylic acid, ethyl ester (0.05 mol.) are slowly added to a solution of 1.5 g. sodium in 100 ml. of alcohol at reflux temperature with stirring. Heating is continued for 3 hours, after completion of the addition. The precipitated sodium chloride is filtered off and the alcohol removed in vacuo. The resulting oily residue, 6-(N-benzyl-N-ethyl)amino-4-ethoxy-2-methyl-5-nitropyridine-3-carboxylic acid, ethyl ester is not further purified. Yield 19 g.

c.
5-Amino-4-ethoxy-6-ethylamino-2-methylpyridine-3-carboxylic acid, ethyl ester 19 g. of crude 6-(N-benzyl-N-ethyl)amino-4-ethoxy-2-methyl-5-nitropyridine-3-carboxylic acid, ethyl ester are dissolved in 100 ml. of butyl alcohol, and 1 g. of palladium on charcoal is added. The mixture is hydrogenated at 3 atmospheres pressure and 100° until no more hydrogen is absorbed. The catalyst is filtered off and the solvent evaporated. The remaining oil, 5-amino-4-ethoxy-6-ethylamino-2-methylpyridine-3-carboxylic acid, ethyl ester is used without further purfication.

d.
2,5-Dimethyl-7-ethoxy-3-ethyl-3H-imidazo[4,5-b]pyridine-6-carboxylic acid, ethyl ester Crude 5-amino-4-ethoxy-6-ethylamino-2-methylpyridine-3-carboxylic acid, ethyl ester is refluxed in acetic acid overnight. The solvent is distilled off and the residue, 2,5-dimethyl-7-ethoxy-3-ethyl-3H-imidazo[4,5-b]pyridine-6-carboxylic acid, ethyl ester is recrystallized from petroleum ether, m.p. 62°–65°.

EXAMPLE 16
7-Ethoxy-3-Ethyl-5-Phenyl-3H-Imidazo[4,5-b]Pyridine-6-Carboxylic Acid, Ethyl Ester By replacing 4,6-dihydroxy-2-methyl-5-nitropyridine-3-carboxylic acid, ethyl ester in Example 1 a with 4,6-dihydroxy-5-nitro-2-phenylpyridine-3-carboxylic acid, ethyl ester, 7-ethoxy-3-ethyl-5-phenyl-3H-imidazo[4,5-b]pyridine-6-carboxylic acid, ethyl ester is obtained.

EXAMPLE 17
7-Ethoxy-5-Methyl-3H-Imidazo[4,5-b]Pyridine-6-Carboxylic Acid Ethyl Ester By replacing methylhydrazine in Example 2 a with hydrazine hydrate, 7-ethoxy-5-methyl-3H-imidazo[4,5-b]-pyridine-6-carboxylic acid, ethyl ester is obtained.

EXAMPLE 18
5-Butyl-7-Ethoxy-3-Ethyl-3H-Imidazo[4,5-b]Pyridine-6-Carboxylic Acid, Butyl Ester By replacing 4,6-dihydroxy-2-methyl-5-nitropyridine-3-carboxylic acid, ethyl ester in Example 1 a with 2-butyl-4,6-dihydroxy-5-nitropyridine-3-carboxylic acid, butyl ester, 5-butyl-7-ethoxy-3-ethyl-3H-imidazo[4,5-b]pyridine-6-carboxylic acid, butyl ester is obtained.

The following additional products of formula I shown in column V are obtained by substituting in Example 1 the reagent indicated in Column I, II, III or IV (no entry in any of columns I, II, III or IV indicates that the same reactant as in Example 1 is used):

| | I | | II | III |
|---|---|---|---|---|
| Example | R | R⁴ | R¹ | R² |
| 19 | $C_3H_7$ | $C_2H_5$ | $CH_3$ | |
| 20 | | | | |
| 21 | $CH_3$ | | —⟨H⟩ (cyclopentyl) | $CH_3$ |
| 22 | | | —⟨H⟩ (cyclohexyl) | |
| 23 | | $C_4H_9$ | —⟨phenyl⟩ | |
| 24 | | | | $C_4H_9$ |
| 25 | | $C_2H_5$ | | |
| 26 | | | | |
| 27 | | | —$CH_2CH_2$—⟨phenyl⟩ | $CH_3$ |
| 28 | $CH_3$ | H | —$CH_2$—⟨phenyl⟩ | |
| 29 | | | | —⟨phenyl⟩ |
| | | | —⟨phenyl⟩ | |

-continued

| Example | | | |
|---|---|---|---|
| 30 | | | —CH$_2$—C$_6$H$_5$ |
| 31 | | | —CH$_2$CH$_2$—C$_6$H$_5$ |
| 32 | H | | |
| 33 | | | |
| 34 | H | | |
| 35 | | | |
| 36 | | | |
| 37 | | | CH$_3$ |
| 38 | | | |
| 39 | | H | |
| 40 | CH$_3$ | CH$_3$ | CH$_3$ |
| 41 | C$_2$H$_5$ | | |
| 42 | | | —C$_6$H$_5$ |
| 43 | | | |

Na—OR$^3$

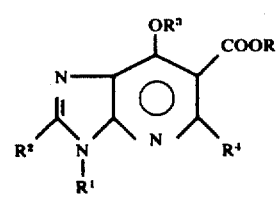

| | IV | | | V | | |
|---|---|---|---|---|---|---|
| Example | R$^3$ | R | R$^1$ | R$^2$ | R$^3$ | R$^4$ |
| 19 | C$_2$H$_5$ | C$_3$H$_7$ | CH$_3$ | H | C$_2$H$_5$ | C$_2$H$_5$ |
| 20 | | C$_2$H$_5$ | | H | C$_2$H$_5$ | CH$_3$ |
| 21 | | CH$_3$ | cyclopentyl-H | CH$_3$ | C$_2$H$_5$ | CH$_3$ |
| 22 | C$_2$H$_5$ | | cyclopentyl-H | H | C$_2$H$_5$ | CH$_3$ |
| | | | —C$_6$H$_5$ | | | |
| 23 | C$_4$H$_9$ | C$_2$H$_5$ | C$_2$H$_5$ | H | C$_4$H$_9$ | C$_4$H$_9$ |
| 24 | | C$_2$H$_5$ | C$_2$H$_5$ | C$_4$H$_9$ | C$_2$H$_5$ | CH$_3$ |
| 25 | C$_7$H$_{15}$ | C$_2$H$_5$ | C$_2$H$_5$ | H | C$_7$H$_{15}$ | C$_2$H$_5$ |
| 26 | | C$_2$H$_5$ | —CH$_2$CH$_2$—C$_6$H$_5$ | H | C$_2$H$_5$ | CH$_3$ |
| 27 | | C$_2$H$_5$ | —CH$_2$—C$_6$H$_5$ | CH$_3$ | C$_2$H$_5$ | CH$_3$ |
| 28 | | CH$_3$ | C$_2$H$_5$ | —C$_6$H$_5$ | C$_2$H$_5$ | H |
| 29 | | C$_2$H$_5$ | C$_2$H$_5$ | H | C$_2$H$_5$ | —C$_6$H$_5$ |
| 30 | CH$_3$ | C$_2$H$_5$ | C$_2$H$_5$ | —CH$_2$—C$_6$H$_5$ | CH$_3$ | CH$_3$ |
| 31 | C$_4$H$_9$ | C$_2$H$_5$ | C$_2$H$_5$ | —CH$_2$CH$_2$—C$_6$H$_5$ | C$_4$H$_9$ | CH$_3$ |
| 32 | —C$_6$H$_5$ | C$_2$H$_5$ | C$_2$H$_5$ | H | —C$_6$H$_5$ | H |
| 33 | 2,4,6-tri-CH$_3$-C$_6$H$_2$— | C$_2$H$_5$ | C$_2$H$_5$ | H | 2,4,6-tri-CH$_3$-C$_6$H$_2$— | CH$_3$ |
| 34 | 4-C$_2$H$_5$-C$_6$H$_4$— | C$_2$H$_5$ | C$_2$H$_5$ | H | 4-C$_2$H$_5$-C$_6$H$_4$— | H |
| 35 | 4-Cl-C$_6$H$_4$— | C$_2$H$_5$ | C$_2$H$_5$ | H | 4-Cl-C$_6$H$_4$— | CH$_3$ |
| 36 | 4-NH$_2$-C$_6$H$_4$— | C$_2$H$_5$ | C$_2$H$_5$ | H | 4-NH$_2$-C$_6$H$_4$— | CH$_3$ |
| 37 | 4-CF$_3$-C$_6$H$_4$— | C$_2$H$_5$ | C$_2$H$_5$ | H | CH$_3$-(4-CF$_3$-C$_6$H$_4$)— | CH$_3$ |

-continued

| # | | | | | | |
|---|---|---|---|---|---|---|
| 38 | (2-Br, methyl-phenyl) | C₂H₅ | C₂H₅ | H | (Br, Br-phenyl) | CH₃ |
| 39 | CH₂—(Br-phenyl) | C₂H₅ | H | H | —CH₂—(Br-phenyl) | CH₃ |
| 40 | —CH₂CH₂—(phenyl) | CH₃ | CH₃ | CH₃ | —CH₂CH₂—(phenyl) | CH₃ |
| 41 | —CH=CH₂ | C₂H₅ | C₂H₅ | H | —CH=CH₂ | C₂H₅ |
| 42 | —CH₂—CH=CH—CH₃ | C₂H₅ | C₂H₅ | (phenyl) | —CH₂—CH=CH—CH₃ | CH₃ |
| 43 | [H] | C₂H₅ | C₂H₅ | H | [H] | CH₃ |

EXAMPLE 44

7-[3-(Dimethylamino)propoxy]-3,5-dimethyl-3H-imidazo[4,5-b]-pyridine-6-carboxylic acid, ethyl ester To a solution of 1.1 g. of 3-dimethylaminopropan-1-ol in 100 ml. of dry benzene are added 4 ml. of a 20% solution of butyl lithium in hexane. The mixture is stirred at room temperature for 15 minutes. After this time, 2.5 g. of 7-chloro-3,5-dimethyl-3H-imidazo[4,5-b]pyridine-6-carboxylic acid, ethyl ester are added and the solution is heated at reflux temperature with stirring for 12 hours. After cooling, the solution is shaken with 50 ml. of a saturated aqueous sodium carbonate solution. The benzene layer is separated, dried with calcium chloride and evaporated to dryness. The remaining oily residue, 7-[3-(dimethylamino)propoxy]-3,5-dimethyl-3H-imidazo[4,5-b]pyridine-6-carboxylic acid, ethyl ester, is purified by distillation, yield 2.2 g. (85%); b.p. 175°–180°/0.01 mm.

EXAMPLE 45

7-[2-(Dimethylamino)ethoxy]-3,5-dimethyl-3H-imidazo[4,5-b]-pyridine-6-carboxylic acid, ethyl ester By replacing the 3-dimethylaminopropan-1-ol in the procedure of Example 44 with 2-dimethylaminoethan-1-ol, 7-[2-(dimethylamino)ethoxy]-3,5-dimethyl-3H-imidazo[4,5-b]pyridine-6-carboxylic acid, ethyl ester is obtained, yield 78%; b.p. 170°–175°/0.01 mm.

What is claimed is:

1. A compound of the formula

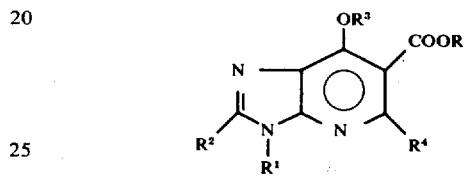

wherein
R is hydrogen or lower alkyl;
$R^1$ is hydrogen, lower alkyl, phenyl, phenyl-lower alkyl or cyclo-lower alkyl;
$R^2$ is hydrogen, lower alkyl, phenyl or phenyl-lower alkyl;
$R^3$ is lower alkyl or lower alkenyl;
$R^4$ is hydrogen, lower alkyl or phenyl; and physiologically acceptable salts thereof.

2. A compound as in claim 1 wherein $R^1$ is lower alkyl.

3. A compound as in claim 1 wherein $R^3$ is lower alkyl.

4. A compound as in claim 1 wherein R and $R^2$ each is hydrogen or lower alkyl; $R^1$ and $R^3$ each is lower alkyl; and $R^4$ is lower alkyl or phenyl.

5. A compound as in claim 1 wherein R, $R^1$, $R^2$, $R^3$ and $R^4$ each is lower alkyl.

6. A compound as in claim 1 wherein R, $R^1$ and $R^4$ each is lower alkyl and $R^2$ is hydrogen.

7. A compound as in claim 1 wherein R and $R^1$ each is ethyl, $R^2$ is hydrogen, $R^4$ is methyl and $R^3$ is lower alkyl.

8. A compound as in claim 7 wherein $R^3$ is ethyl.

9. A compound as in claim 7 wherein $R^3$ is 1-methylethyl.

10. A compound as in claim 7 wherein $R^3$ is butyl.

11. A compound as in claim 7 wherein $R^3$ is 3-methylbutyl.

12. A compound as in claim 1 wherein R and $R^3$ each is ethyl, $R^1$ and $R^4$ each is methyl and $R^2$ is hydrogen.

13. A compound as in claim 1 wherein R and $R^3$ each is ethyl, $R^1$ is butyl, $R^2$ is hydrogen and $R^4$ is methyl.

14. A compound as in claim 1 wherein R is ethyl, $R^1$ and $R^4$ each is methyl, $R^2$ is hydrogen and $R^3$ is 3-methylbutyl.

* * * * *